United States Patent
Champagne et al.

(10) Patent No.: US 12,048,464 B2
(45) Date of Patent: *Jul. 30, 2024

(54) INTRAMEDULLARY THREADED NAIL FOR RADIAL CORTICAL FIXATION

(71) Applicant: ExsoMed Corporation, Aliso Viejo, CA (US)

(72) Inventors: Lloyd P. Champagne, Phoenix, AZ (US); Jozef Zoldos, Phoenix, AZ (US); Richard Thomas Briganti, Bala Cynwyd, PA (US); Andrew J. Leither, Akron, OH (US)

(73) Assignee: ExsoMed Corporation, Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,177

(22) Filed: Feb. 16, 2024

(65) Prior Publication Data

US 2024/0188999 A1    Jun. 13, 2024

Related U.S. Application Data

(60) Continuation of application No. 17/454,028, filed on Nov. 8, 2021, now Pat. No. 11,903,623, which is a
(Continued)

(51) Int. Cl.
*A61B 17/72* (2006.01)
*A61B 17/86* (2006.01)
*A61B 17/00* (2006.01)

(52) U.S. Cl.
CPC ...... *A61B 17/7291* (2013.01); *A61B 17/8635* (2013.01); *A61B 17/864* (2013.01); *A61B 17/8645* (2013.01); *A61B 2017/00867* (2013.01)

(58) Field of Classification Search
CPC .................................................. A61B 17/7291
See application file for complete search history.

(56) References Cited

U.S. PATENT DOCUMENTS 1,741,279 A    12/1929    Bowman
2,037,586 A    4/1936    Olson
(Continued)

FOREIGN PATENT DOCUMENTS

CH    643131    5/1984
CH    646858    12/1984
(Continued)

OTHER PUBLICATIONS

Examination Report No. 1 corresponding to related Australian Patent Application No. 2018328102 dated Aug. 25, 2022, 3 pages.
(Continued)

*Primary Examiner* — Christian A Sevilla
(74) *Attorney, Agent, or Firm* — K&L Gates LLP

(57) ABSTRACT

The present invention relates to a device and system for fixation of intra-articular and extra-articular fractures and non-unions of small bones and other small bone fragments, and more particularly to a threaded nail with a robust length and a trailing end with a cutting tip and longitudinal cutting flutes and a stepped diameter with cutting flutes at the transition point, and an optional cannulation along the central longitudinal axis of the nail.

10 Claims, 4 Drawing Sheets

Related U.S. Application Data division of application No. 16/805,485, filed on Feb. 28, 2020, now Pat. No. 11,191,576, which is a continuation of application No. PCT/US2018/049342, filed on Sep. 4, 2018.

(60) Provisional application No. 62/554,123, filed on Sep. 5, 2017.

(56) References Cited

U.S. PATENT DOCUMENTS

| | | |
|---|---|---|
| 2,210,455 A | 8/1940 | Hosking |
| 2,217,951 A | 10/1940 | Hosking |
| 2,229,892 A | 1/1941 | Hosking |
| 2,242,003 A | 5/1941 | Lorenzo |
| 3,078,900 A | 2/1963 | Walker |
| 3,275,055 A | 9/1966 | Gutshall |
| 3,397,699 A | 8/1968 | Kohl |
| 3,717,146 A | 2/1973 | Halloran |
| 4,016,874 A | 4/1977 | Maffei |
| 4,175,555 A | 11/1979 | Herbert |
| 4,350,465 A | 9/1982 | Lovisek |
| 4,380,414 A | 4/1983 | Capuano |
| 4,456,005 A * | 6/1984 | Lichty ............... A61B 17/8685 606/328 |
| 4,463,753 A | 8/1984 | Gustilo |
| 4,471,777 A | 9/1984 | McCorkle |
| 4,584,722 A | 4/1986 | Levy et al. |
| 4,608,965 A | 9/1986 | Anspach |
| 4,764,066 A | 8/1988 | Terrell |
| 4,781,191 A | 11/1988 | Thompson |
| 4,812,095 A | 3/1989 | Piacenti |
| 4,820,235 A | 4/1989 | Weber et al. |
| 4,842,463 A | 6/1989 | Landt |
| 4,901,717 A | 2/1990 | Moore et al. |
| 4,909,789 A | 3/1990 | Taguchi et al. |
| 4,950,270 A | 8/1990 | Bowman et al. |
| 5,019,079 A * | 5/1991 | Ross ................... A61B 17/863 411/389 |
| 5,061,283 A | 10/1991 | Silvestrini |
| 5,180,382 A * | 1/1993 | Frigg .................. A61B 17/863 606/65 |
| 5,234,299 A | 8/1993 | Giannuzzi |
| 5,259,398 A * | 11/1993 | Vrespa ................ A61C 8/0089 411/413 |
| 5,312,255 A | 5/1994 | Bauer |
| 5,345,927 A | 9/1994 | Bonutti |
| D356,868 S * | 3/1995 | Broberg .................. D24/156 |
| 5,443,466 A | 8/1995 | Shah |
| 5,522,846 A | 6/1996 | Bonutti |
| 5,645,545 A | 7/1997 | Bryant |
| 5,667,510 A | 9/1997 | Combs |
| 5,690,633 A | 11/1997 | Taylor et al. |
| 5,735,653 A | 4/1998 | Schiefer et al. |
| 5,827,285 A * | 10/1998 | Bramlet ............... A61B 17/80 606/328 |
| 5,840,078 A | 11/1998 | Yerys |
| 5,853,413 A | 12/1998 | Carter et al. |
| 5,964,766 A | 10/1999 | Shaw |
| 6,030,162 A | 2/2000 | Huebner |
| 6,187,007 B1 | 2/2001 | Frigg |
| 6,221,006 B1 | 4/2001 | Dubrul et al. |
| 6,231,319 B1 | 5/2001 | Iida et al. |
| 6,231,413 B1 | 5/2001 | Tsukamoto |
| 6,306,140 B1 | 10/2001 | Siddiqui |
| 6,394,725 B1 | 5/2002 | Dicke |
| 6,475,242 B1 | 11/2002 | Bramlet |
| 6,517,541 B1 | 2/2003 | Sesic |
| 6,592,623 B1 | 7/2003 | Bowlin et al. |
| 6,607,530 B1 | 8/2003 | Carl et al. |
| 6,808,526 B1 | 10/2004 | Magerl et al. |
| 7,037,309 B2 | 5/2006 | Well et al. |
| 7,041,106 B1 | 5/2006 | Carver et al. |
| 7,063,491 B2 | 6/2006 | French |
| 7,334,976 B2 | 2/2008 | Dicke |
| 7,465,135 B2 | 12/2008 | Fritsch |
| 7,507,242 B2 | 3/2009 | Triplett et al. |
| 7,604,659 B2 | 10/2009 | Lee |
| 7,708,738 B2 | 5/2010 | Fourcault et al. |
| 7,766,942 B2 | 8/2010 | Patterson |
| 7,988,724 B2 | 8/2011 | Salahieh et al. |
| 8,011,866 B2 | 9/2011 | Harris |
| 8,075,604 B2 * | 12/2011 | Denis ................. A61B 17/7041 606/315 |
| 8,157,803 B1 | 4/2012 | Zirkle, Jr. |
| 8,348,575 B2 | 1/2013 | Walther |
| 8,398,687 B2 | 3/2013 | Vasta et al. |
| 8,414,648 B2 | 4/2013 | Reiley |
| 8,419,776 B2 | 4/2013 | Prandi et al. |
| 8,518,042 B2 | 8/2013 | Winsow et al. |
| 8,568,462 B2 | 10/2013 | Sixto et al. |
| 8,597,337 B2 | 12/2013 | Champagne |
| 8,608,783 B2 | 12/2013 | Graham et al. |
| 8,715,326 B2 * | 5/2014 | Champagne ....... A61B 17/8685 606/328 |
| 8,814,918 B2 | 8/2014 | Orbay et al. |
| 8,852,253 B2 | 10/2014 | Mafi |
| 8,888,429 B2 | 11/2014 | Pamer |
| 8,906,075 B2 | 12/2014 | Conley et al. |
| 9,017,404 B2 | 4/2015 | Champagne et al. |
| 9,046,120 B2 | 6/2015 | Phua |
| 9,055,986 B1 | 6/2015 | Whipple et al. |
| 9,086,088 B2 | 7/2015 | Walther |
| 9,175,715 B2 | 11/2015 | Babej |
| 9,265,600 B2 | 2/2016 | Niese |
| 9,480,515 B2 | 11/2016 | Champagne |
| 9,539,084 B2 | 1/2017 | Champagne |
| 10,098,680 B2 | 10/2018 | Champagne |
| 2001/0049529 A1 | 12/2001 | Cachia et al. |
| 2002/0045897 A1 | 4/2002 | Dixon et al. |
| 2002/0055747 A1 | 5/2002 | Cano et al. |
| 2002/0055749 A1 | 5/2002 | Esnouf et al. |
| 2002/0143337 A1 | 10/2002 | Orbay et al. |
| 2002/0198527 A1 | 12/2002 | Muckter |
| 2003/0014071 A1 | 1/2003 | Leung |
| 2003/0028193 A1 | 2/2003 | Weil et al. |
| 2003/0083661 A1 | 5/2003 | Orbay et al. |
| 2003/0130735 A1 | 7/2003 | Rogalski |
| 2004/0193217 A1 | 9/2004 | Lubbers |
| 2004/0210227 A1 | 10/2004 | Trail et al. |
| 2004/0260288 A1 | 12/2004 | Means |
| 2004/0260291 A1 | 12/2004 | Jensen |
| 2005/0075642 A1 | 4/2005 | Felt et al. |
| 2005/0107791 A1 | 5/2005 | Manderson |
| 2005/0143735 A1 | 6/2005 | Kyle |
| 2006/0129153 A1 | 6/2006 | Klaue et al. |
| 2006/0149249 A1 | 7/2006 | Mathoulin et al. |
| 2006/0165506 A1 | 7/2006 | Panasik |
| 2006/0195099 A1 | 8/2006 | Bottlang |
| 2006/0276790 A1 | 12/2006 | Dawson |
| 2007/0027547 A1 | 2/2007 | Rydell et al. |
| 2007/0135816 A1 | 6/2007 | Kropf et al. |
| 2007/0282342 A1 | 12/2007 | Niederberger et al. |
| 2007/0299449 A1 | 12/2007 | Allinniemi et al. |
| 2008/0183220 A1 | 7/2008 | Glazer |
| 2008/0219801 A1 | 9/2008 | Toenjes |
| 2008/0249547 A1 | 10/2008 | Dunn |
| 2008/0249574 A1 | 10/2008 | McCombs et al. |
| 2009/0062868 A1 | 3/2009 | Casutt |
| 2009/0210016 A1 | 8/2009 | Champagne |
| 2009/0299369 A1 | 12/2009 | Orbay et al. |
| 2010/0069970 A1 | 3/2010 | Lewis et al. |
| 2010/0106254 A1 | 4/2010 | Delsignore |
| 2010/0121136 A1 | 5/2010 | Champagne |
| 2010/0130978 A1 | 5/2010 | Orbay et al. |
| 2010/0211115 A1 | 8/2010 | Tyber et al. |
| 2010/0278614 A1 | 11/2010 | Bickford |
| 2010/0312286 A1 | 12/2010 | Dell'Oca |
| 2010/0324556 A1 | 12/2010 | Tyber et al. |
| 2011/0009865 A1 | 1/2011 | Orfaly |
| 2011/0034925 A1 | 2/2011 | Tipirneni et al. |
| 2011/0130794 A1 | 6/2011 | Vaidya |
| 2011/0293387 A1 | 12/2011 | Chang |
| 2012/0083847 A1 | 4/2012 | Heubner et al. |

(56) References Cited

U.S. PATENT DOCUMENTS

| | | |
|---|---|---|
| 2012/0136398 A1 | 5/2012 | Mobasser |
| 2012/0191140 A1 | 7/2012 | Bonutti |
| 2012/0221104 A1 | 8/2012 | Altman et al. |
| 2012/0253464 A1 | 10/2012 | Hwang et al. |
| 2012/0253465 A1 | 10/2012 | Missos |
| 2013/0012987 A1 | 1/2013 | Klein et al. |
| 2013/0053961 A1 | 2/2013 | Darwin et al. |
| 2013/0060333 A1 | 3/2013 | Gonzalez |
| 2013/0131699 A1 | 5/2013 | Jiang et al. |
| 2013/0138123 A1 | 5/2013 | Stone et al. |
| 2013/0165979 A1 | 6/2013 | Greenberg et al. |
| 2013/0190872 A1 | 7/2013 | Makower et al. |
| 2013/0197592 A1 | 8/2013 | Mafi |
| 2013/0245626 A1 | 9/2013 | Lavi et al. |
| 2013/0245700 A1 | 9/2013 | Choinski |
| 2013/0245762 A1 | 9/2013 | Van Kampen et al. |
| 2013/0261662 A1 | 10/2013 | Mayer et al. |
| 2013/0274814 A1 | 10/2013 | Weiner et al. |
| 2013/0274879 A1 | 10/2013 | Champagne et al. |
| 2013/0282058 A1 | 10/2013 | ElAttrache et al. |
| 2013/0325011 A1 | 12/2013 | Cleveland et al. |
| 2014/0025124 A1 | 1/2014 | Champagne et al. |
| 2014/0067063 A1 | 3/2014 | Bonutti |
| 2014/0257349 A1 | 9/2014 | Sudekum |
| 2014/0276846 A1 | 9/2014 | Mauldin |
| 2014/0277191 A1 | 9/2014 | Evans et al. |
| 2014/0336712 A1 | 11/2014 | Strnad et al. |
| 2015/0066060 A1 | 3/2015 | Bojarski |
| 2015/0088136 A1 | 3/2015 | Kotuljac et al. |
| 2015/0094722 A1 | 4/2015 | Champagne et al. |
| 2015/0094724 A1 | 4/2015 | Champagne et al. |
| 2015/0094777 A1 | 4/2015 | Champagne et al. |
| 2015/0112342 A1 | 4/2015 | Penzimer et al. |
| 2015/0173737 A1 | 6/2015 | Champagne et al. |
| 2015/0182325 A1 | 7/2015 | Champagne et al. |
| 2015/0201984 A1 | 7/2015 | Orbay et al. |
| 2016/0022339 A1 | 1/2016 | Machida |
| 2016/0030097 A1 | 2/2016 | Mildner et al. |
| 2016/0256290 A1 | 9/2016 | Seavey et al. |
| 2016/0296263 A1 | 10/2016 | Champagne et al. |
| 2016/0296264 A1 | 10/2016 | Champagne et al. |
| 2016/0338748 A1 | 11/2016 | Champagne et al. |
| 2017/0014170 A1 | 1/2017 | Fallin et al. |
| 2017/0027577 A1 | 2/2017 | Kubiak et al. |
| 2017/0035553 A1 | 2/2017 | Champagne et al. |
| 2017/0049167 A1 | 2/2017 | Champagne et al. |
| 2017/0189090 A1 | 7/2017 | Champagne et al. |
| 2017/0196609 A1 | 7/2017 | Champagne et al. |
| 2017/0325827 A1 | 11/2017 | Champagne et al. |
| 2018/0021124 A1 | 1/2018 | Champagne et al. |
| 2018/0263669 A1* | 9/2018 | Peterson ............ A61B 17/8605 |
| 2020/0022817 A1* | 1/2020 | Crossgrove .......... A61B 17/863 |
| 2022/0346850 A1 | 11/2022 | Clark et al. |

FOREIGN PATENT DOCUMENTS

| | | |
|---|---|---|
| DE | 2713386 | 11/1978 |
| DE | 102007003645 | 7/2008 |
| DE | 202013101135 U1 | 6/2014 |
| EP | 0597223 | 5/1994 |
| EP | 1378205 | 1/2004 |
| EP | 2606843 | 6/2013 |
| GB | 2007099 | 5/1979 |
| GB | 2181356 | 4/1987 |
| WO | 1997/33537 | 9/1997 |
| WO | 2004/093700 | 4/2004 |
| WO | 2005/092226 | 10/2005 |
| WO | 2006/105935 | 12/2006 |
| WO | 2007/081601 | 7/2007 |
| WO | 2007/109140 | 9/2007 |
| WO | 2008/063156 | 5/2008 |
| WO | 2008/064037 A2 | 5/2008 |
| WO | 2008064037 A2 | 5/2008 |
| WO | 2010/151589 | 12/2010 |
| WO | 2012/050424 | 4/2012 |
| WO | 2012074991 A1 | 6/2012 |
| WO | 2014/011933 | 1/2014 |
| WO | 2015100149 A1 | 7/2015 |
| WO | 2015/050895 | 9/2015 |
| WO | 2015/050896 | 9/2015 |
| WO | 2015/050898 | 9/2015 |
| WO | 2015/050900 | 9/2015 |
| WO | 2015/050902 | 9/2015 |
| WO | 2015147847 A1 | 10/2015 |
| WO | 2016/186847 | 11/2016 |
| WO | 2019050833 A1 | 3/2019 |

OTHER PUBLICATIONS

Israeli Office Action corresponding to related Israeli Patent Application No. 273011 dated Dec. 26, 2022, 4 pages.

Japanese Office Action corresponding to related Japanese Patent Application No. 2020-534810 dated Feb. 16, 2023, 8 pages.

European Office Action corresponding to related European Patent Application No. 18854272.4 dated Mar. 17, 2023, 5 pages.

Israeli Office Action corresponding to related Israeli Patent Application No. 273011 dated Dec. 10, 2023, 4 pages.

Partial Supplementary Search Report in corresponding European Patent Application No. 18854272.4, dated Jun. 28, 2021, in 14 pages.

Extended Search Report in corresponding European Patent Application No. 18854272.4, dated Sep. 27, 2021, in 14 pages.

Skeletal Dynamics, LLC, "Surgical Technique Guide—REDUCT™ headless compress screw," Copyright 2018, in 8 pages.

Stryker Osteosynthesis, "Fixos Forefoot & Mid-foot Screw System" Product Information, Copyright 2015, in 28 pages.

Zimmer Biomet, "MAX VPC™ Screw System—Surgical Technique," Copyright 2016, in 24 pages.

Zimmer Biomet, "Zimmer® Herbert™ Cannulated Bone Screw" Product Information, Copyright 2015, in 4 pages.

International Search Report from corresponding International Patent Application No. PCT/US2018/049342, dated Oct. 19, 2018, in 2 pages.

Written Opinion from corresponding International Patent Application No. PCT/US2018/049342, dated Oct. 19, 2018, in 7 pages.

International Preliminary Report on Patentability from corresponding International Patent Application No. PCT/ US2018/049342, dated Mar. 10, 2020, in 8 pages.

Acumed LLC. "Acutrak 2 Headless Compression Screw System." Retrieved from the Internet on Feb. 21, 2024. <https://www.acumed.net/products/screw-pin/acutrak-2-headless-compression-screw-system/>.

Acumed LLC. "Acutrak 3 Headless Compression Screw System." Retrieved from the Internet on Feb. 21, 2024. <https://www.acumed.net/products/screw-pin/acutrak-3-headless-compression-screw-system/>.

Arthrex, Inc. "Compression FT Screws." Retrieved from the Internet on Feb. 21, 2024. <https://www.arthrex.com/hand-wrist/compression-ft-screws?currenttab=resources#allResources>.

"Arthrex Minimally Invasive Bunionectomy: Surgical Technique". Naples, Florida: Arthrex, Inc., 2023. <https://www.arthrex.com/resources/LT1-000195-en-US/arthrex-minimally-invasive-bunionectomy?referringteam=foot_and_ankle>. Pamphlet.

"For Fixation of Small Bones and Small Bone Fragments: 2.4 mm and 3.0 mm Headless Compression Screws—Surgical Technique". West Chester, Pennsylvania: DePuy Synthes, 2006-2017. <https://www.jnjmedtech.com/sites/default/files/user_uploaded_assets/pdf_assets/2019-01/DSUSTRM09161087_2-4_3mmHeadlessCompScr_TG_150dpi.pdf>. Pamphlet.

Fusion Orthopedics. "FuzeFix Max FT." Retrieved from the Internet on Feb. 21, 2024. <https://fusionorthopedics.com/products/fuzefixmaxft/>.

"Headless Compression and Twist-Off Screws: Surgical Technique". Warsaw, Indiana: Zimmer Biomet, 2018. <https://www.zimmerbiomet.com/content/dam/zb-corporate/en/education-resources/surgical-techniques/specialties/foot-&-ankle/headless-compression-&-twist-off-screws/19902USenHeadlessCompressionandTwistOffScrewsSurgTech1.pdf> Pamphlet.

(56) References Cited

OTHER PUBLICATIONS

"I.B.S. (Innovative Bone Synthesis™): Mid & Hindfoot Screw System—Compression Screw, Neutralization Screw". Ecully, France: In2Bones SAS, 2014. <https://www.in2bones.com/BRO/ST-MHFScrews-EN-042014-P.pdf>. Pamphlet.

"MAX VPC™ Screw System". Warsaw, Indiana: Zimmer Biomet, 2016-2021. <https://www.zimmerbiomet.com/content/dam/zb-corporate/en/products/specialties/trauma/max-vpc-screw-system/0925.2-GLBL-en_MAX%20VPC_Screw_System_Brochure-Digital.pdf>. Pamphlet.

"Trilliant™ Tiger Headless Cannulated Screw System". Houston, Texas: DJO, LLC, 2021. <https://www.djoglobal.com/sites/default/files/Tiger%20Headless%20Brochure%20900-00-013%20Rev%20N.pdf>. Pamphlet.

Wikipedia. "Herbert screw." Retrieved from the Internet on Feb. 21, 2024. <https://en.wikipedia.org/wiki/Herbert_screw>.

Examination Report No. 1 from corresponding Australian Patent Application No. 2023202584, mailed Feb. 20, 2024. 4 pages.

\* cited by examiner

INTRAMEDULLARY THREADED NAIL FOR RADIAL CORTICAL FIXATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 17/454,028, filed Nov. 8, 2021, entitled INTRAMEDULLARY THREADED NAIL FOR RADIAL CORTICAL FIXATION, which is a divisional of U.S. patent application Ser. No. 16/805,485, filed Feb. 28, 2020, entitled INTRAMEDULLARY THREADED NAIL FOR RADIAL CORTICAL FIXATION, now U.S. Pat. No. 11,191,576, which is a continuation of International Patent Application No. PCT/US2018/049342, filed Sep. 4, 2018, entitled INTRAMEDULLARY THREADED NAIL FOR RADIAL CORTICAL FIXATION, which claims the benefit of priority to U.S. Provisional Patent Application No. 62/554,123, filed Sep. 5, 2017, entitled INTRAMEDULLARY THREADED NAIL, the entirety of which is hereby incorporated by reference herein and should be considered part of this specification.

FIELD OF THE INVENTION

The present invention relates to a device and system for fixation of fractures and non-unions of small bones and other small bone fragments, and more particularly to a threaded nail with a robust length and a headless leading end with a torque driving recess and a trailing end with a cutting tip and longitudinal cutting flutes, and an intermediate stepped diameter with cutting flutes at the transition point, Optionally, the device includes a cannulation along the central longitudinal axis of the nail. This intramedullary nail provides for full shaft-length and internally circumferential cortical fixation in particular for use in the metacarpals and metatarsals. Thus, the implant achieves at least a frictional fit circumferentially with the internal cortex for at least 60%+/−15% of the intramedullary canal length by means of engagement with a penetrating supplemental spiral thread along at least 80%+/−15% of the length of the implant.

BACKGROUND OF THE INVENTION

Trauma to the mid-hand and mid-foot can have life-changing effects for the victim as a result of loss of function, disfiguration, and even the lengthy and onerous treatment protocols. It's hard and sometimes impossible to do without the use of a foot or hand, and in particular, when one is living "hand to mouth".

Current methods of treatment include internal fixation with surgery, like plating systems and wire fixation or in the case of non-displaced fractures, casting the hand or foot without surgical intervention. These treatments involve a substantial period, i.e., several weeks or months, in which the injured hand or foot is immobilized. However, serious problems with adhesions, loss of muscle, proprioception and nerve health, can result from dis-use for these periods of time. Moreover, beyond the side effects of the treatment protocol, there are problems with compliance and with the issues of daily living that result from not being able to use a hand or foot for these prolonged periods of time.

While it is possible for hand and foot accidents to occur during various activities, including traffic accidents, firearm mis-fire, and extreme sport activities, there is a greater correlation of the risk for such traumatic events in manual and low wage jobs. Thus, the incidence and the effects of such accidents are skewed to jobs on the lower end of the pay-scale and may often involve workers who are already at economic risk. Thus, victims of hand or foot trauma will often either resort to non-compliance involving the early use of the injured limb, or in some instances will suffer the loss of income, including the loss of a job altogether, which sets off a spiraling decline in the ability to "make ends meet", expanding the risk from the injury to the loss of house and home and family stability.

Finally, it should be noted that the hand is paramount to every aspect of our humanity and is instrumental in dictating and defining our relationship to our world. Injury to the hand hinders that relationship and our perception of our role in that world, especially in cases where the hand is disfigured, or appears to be disabled. Our hands are constantly in view to ourselves and to the world, and debilitating scars or irregularities such as scars, and even the Frankenstein-like outlines of surgical hardware on the mid-hand, are visible and painful reminders of a traumatic event and its aftermath.

The prior art orthopedic implants for use in small bones in the arms and legs have a set of criteria that differs from those of the long bones and large joints. These bones, (generally in the elbow and below and the knee and below), tend to be smaller in diameter and present a differing ratio of cortical to cancellous bone, as well as the issues of covering soft tissue and a relatively large nexus of tendons, ligaments and nerves, to complicate surgical techniques. The present invention is intended to answer these issues, and to provide a solution to surgical fixation of broken or fractured small bones through a threaded nail intended for intramedullary fixation and most importantly, allowing a swift return to daily living, and reduced disability, pain, and rehabilitation.

One typical small bone implant location is the hand or foot, and in particular in the metacarpals and metatarsals. The structure of the hand is composed of the scaphoid and other carpal bones which meet with the radius and the ulna at the wrist joint, the metacarpals, and phalanges. The back of the hand includes the metacarpals, and a metacarpal connects each finger and thumb to the hand, while the fingers and thumb are formed of bones called phalanges. The connection of the phalanges to the metacarpals is called a "knuckle" joint or metacarpophalangeal joint (MCP joint), and acts like a hinge when the fingers or thumb are bent. In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint. The joints are covered on the ends with articular cartilage. The foot has an analogous structure, with the talus interfacing between the tibia and the fibula on the leg, and the calcaneus on the foot, and the mid-foot being comprised of the tarsals, including the cuneiforms, (i.e., the cuboid and the navicular bones,) the metatarsals, and the phalanges.

Damage to these bones of the extremities may occur as a result of a sprain or fracture or trauma and typically following reduction to re-align a damaged bone, it should be stabilized in position to allow it to heal in that position.

In the past, a surgical procedure to stabilize these broken bones has involved drilling a pilot hole and insertion of a k-wire or smooth nail along the length of the bone to hold it in position while the bone heals. An opening is first formed in the metacarpal bone, wherein the opening extends through the fracture and the nail is positioned by wedging it in the opening through the soft cancellous intermediate bone so that the nail provides stability for the parts of the bone on either side of the fracture. After a certain period, a second surgery is required to remove the nail from the bone. Problems with this procedure are that, because it is not anchored in the bone and in fact, mostly interfaces with the spongy central bone pulp, it can migrate through the metacarpal bone and into surrounding tissue. Sometimes this can result in damage to soft tissue, such as a severed or damaged tendon or cartilage, and/or cause pain. Another problem with the nail is that, because it can migrate, a second surgery is required to remove it. Additionally, the proximal end of pins and nails can cause tendon irritation, tendon rupture or skin irritation and infection.

One theoretical solution to this problem is to insert a screw into the bone however, the torque required to place a screw into the length of a metacarpal bone (which is a relatively thin, delicate but brittle bone) is high. Such a procedure would be lengthy, and there would be a possibility of bone damage, or damage to the driving head of the screw, which could prevent complete insertion into the opening formed in the bone. Current screws are not designed specifically for intramedullary placement. For instance, the current screws are frequently not long enough, nor do they account for the narrowed waist of the metacarpal or metatarsal bones.

Thus, the present invention is intended for fixation of intra-articular and extra-articular fractures and non-unions of small bones and small bone fragments; including for example, arthrodesis of small joints; bunionectomies and osteotomies, including scaphoid and other carpals bones, metacarpals, tarsals, metatarsals, patella, ulnar, styloid, capitellum, radial head and radial styloid, and is preferably intended for intramedullary fixation of metacarpal and phalangeal fractures to provide surgeons with a reliable solution through a simple approach. The robust length offering, (more than 3.5 centimeters, and preferably more than 4 centimeters, or 5 centimeters+/−1 or 0.5 centimeters, or even up to 7.5 centimeters), with large length to diameter ratio (more than 15:1, and preferably more than 20:1), and with a differential diameter (having a leading section at a smaller diameter of 3-5 mm, and a trailing length towards the nail head, of from 0.4-2 mm smaller, with good examples of 3.2/3.6 or 4.0/4.5), accurately fits native metacarpal and phalangeal locations to create a strong, stable fixation and precise reduction. Moreover, the invention is intended to fill the intramedullary canal along substantially all its length (i.e., more that 45%, or preferably more than 50%, and preferably more than 60%, or 70% and up to 80% or 98% by length). The design includes a leading, meaning away from the nail end, section having a smaller outer diameter of the root and also of the thread crest at that section, but a relatively constant internal cannulation where the leading section is from 40-60% of the length. The larger diameter section reinforces the area next to the torque receiving end of the nail so that the greater material allows transmission of the torque through the device, and the cutting flutes in the transition section between the dual diameters helps to keep the smaller leading portion from collapsing on itself. Thus, the device is designed to allow both insertion and removal by screwing or unscrewing the implant into the intramedullary canal.

In addition, the invention is unique as it is designed to capture internal cortical bone so that not only does the nail extend a substantial distance of the length of the shaft (at least 60% including penetration past the isthmus), it also is used so that is achieves "radial" or "circumferential" fixation within the canal, and preferably, achieves 360° internal circumferential cortical fixation. This is novel for the metacarpal application since the metacarpals (and metatarsals) include a narrowed waist area, the "isthmus" of the metacarpal (and metatarsals). Past screws and intramedullary implants are not designed to engage with sufficient length or to grab the internal walls of the canal circumferentially over substantial distance of the length, but the current design includes a stepped diameter with a leading cutting tip and an intermediate cutting feature that allows the invention to ream the canal to size as it is advanced through the canal. Thus, the canal is prepped for circumferential cortical fixation, which is unique to the present invention and refers to the use of an implant that includes a surface that is fixed to the internal cortical wall or of the intramedullary shaft, in particular of the metacarpal of the metatarsal. The nail is intended to avoid applying a compressive force along the length of the nail, and can be used in instances in which there is a void in the bone or missing bone fragments and nail stabilizes the remaining bone fragments with a gap to restore the length of the metacarpal. The nail is dual diameter with both leading-diameter and trailing-diameter sections substantially cylindrical and, importantly, not tapered or conical to permit the device to maintain contact with the hole in the canal during removal and to ease removal by unscrewing the nail.

The present invention can be used in a procedure that lets the patient return to work in a short period of time, from two weeks to the next day, including jobs ranging from manual labor, care-giver, professional musician, artist, and professional athlete. This return to functional living, and the decrease in down-time, and rehabilitation and risk to daily living is a huge societal saving.

SUMMARY OF THE INVENTION

The present invention solves the problems associated with repairing a metacarpal or metatarsal fracture or dislocation by providing a device that is a unique combination of a nail and a screw, which can be inserted into the bone without damaging the bone because it is sized and shaped to achieve circumferential intramedullary cortical fixation and to support the bone from the inside. (even when there's a bone gap of from 0 up to 2, 2.5, or even 3 cm along the length of a damaged metacarpal), to fit the narrowed portion of these bones by providing at least one stepped diameter and a fluted transition between the diameters, by providing a headless design with a uniform lead(s) which avoids compression and which can be seated below the surface of the bone to avoid the irritation that can result from a proud portion; by providing for a cannulated surgical technique with an intramedullary implant designed to minimize soft tissue, cartilage and vascular damage upon insertion; and to facilitate early, active mobilization post-operative protocols for accelerated healing and earlier return to work.

Further, as the device achieves radial internal fixation, the device is secured within the bone, which eliminates migration and eliminates the need for a second operation to remove the device. Thus, the device provides a cannulated cylindrical core having an outer exterior surface along its length, (from 35 to 75, or even as long as lengths to 120 or 130 mm) that defines an inner diameter (minor diameter) relative to the lateral edge of a threaded portion which defines an outer diameter (major diameter). The design includes one or more stepped portion which allow for an increase in the trailing portion of at least the outer diameter or the inner diameter, and more preferably of both the outer diameter and the inner diameter. The transition area also includes longitudinal cutting flutes (2-5 of 3 to 10 mm length) to account for this increase at a length of the nail (i.e., from 25% to 75%, and preferably 35% to 60%, of the distance of the length from the trailing end) which allows a clearance of the narrowed or "waisted" portion of the bone. The cannulation is generally a constant diameter (for ease of manufacture) through the length of the nail, but could include a dual diameter which might include an over grind at the larger diameter or trailing end of the nail which includes the torque driving feature, such as an internal or external hexagon or hexalobe configuration.

The device includes a leading portion that has 2-5 cutting teeth on the beveled leading tip, and along the long side, also includes additional longitudinal flutes, which, as are the other flutes, intended to provide for reaming away of the cancellous intramedullary material and for scoring of the inner surface of the intramedullary channel, as well as a place for additional cancellous material to reside during surgery.

The thread defined between the outer diameter and the inner diameter can suitably include a right handed single start thread with a pitch of from 3 to 5 mm, and preferably at least 4.0 mm+/−0.25, or a dual lead thread of the same lead value and a pitch value half of the lead value with a secondary thread having a lower height, i.e., from 40% to 75% or 50%+/−5% of the height of the primary thread. The leading and following flanks of the threads together form an angle of 5° to 60°, and preferably 15°+10°, and are connected by a thread crest of length 0.05 to 0.2 mm which is separated from the root diameter by a thread depth of 0.2 mm to 0.8 mm.

At its first end, or trailing end, the device includes a driving recess capable of being driven by a suitable driver into the opening, such as a hexalobe or a T10 drive recess, to generate significant torque to bite into the cortical bone and avoid harm to the lower material narrower leading end of the nail.

DETAILED DESCRIPTION OF THE INVENTION

Figure 1:
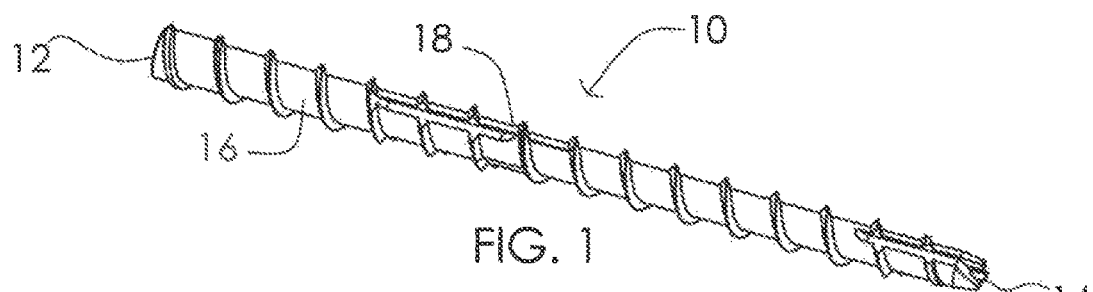
FIG. 1 is a top side view of a device in accordance with the invention.
Figure 2:
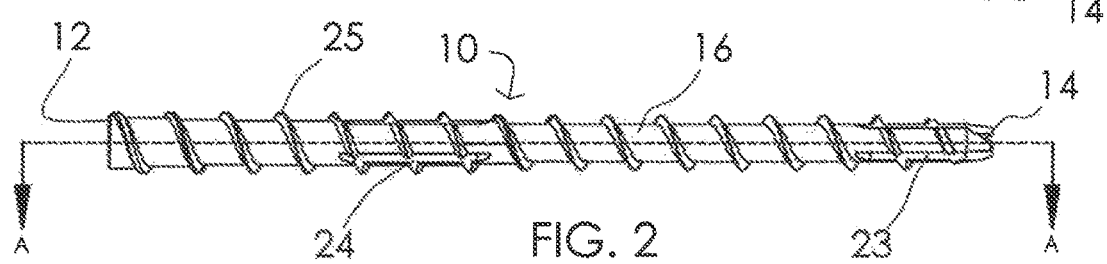
FIG. 2 is a side view of the device of FIG. 1.
Figure 3:
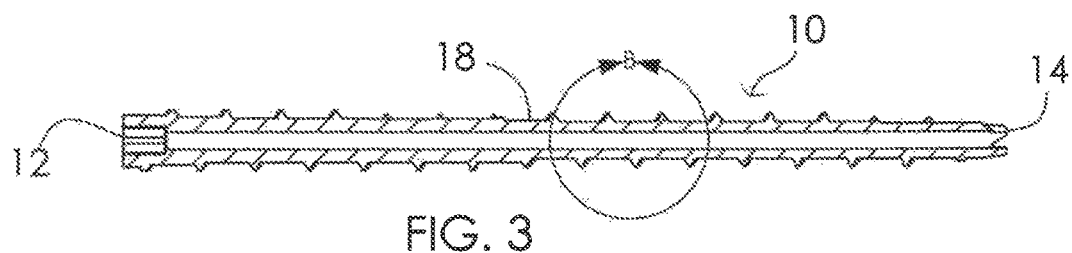
FIG. 3 is a cross-section of the device of FIG. 1 taken along line A-A.
Figure 4:
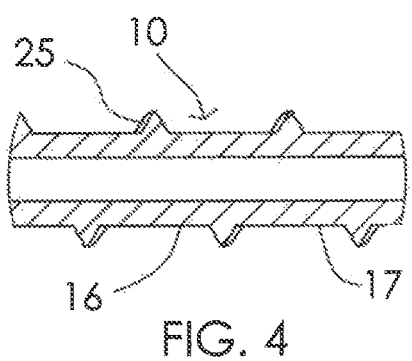
FIG. 4 is a detail of FIG. 3 showing the thread characteristics and a detail of the thread shape.
Figure 5:
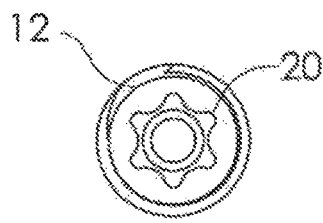
FIG. 5 is an end view of the proximal view of the device of FIG. 1.
Figure 6:
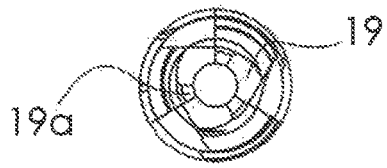
FIG. 6 is an end view of the distal tip of the device of FIG. 1.
Figure 7:
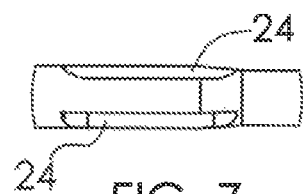
FIG. 7 is a side view detail of the transition section of the blank from which the invention is made and showing the intermediate cutting flutes of FIG. 1.
Figure 8:
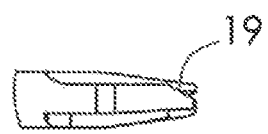
FIG. 8 is a side view detail of the distal end of the blank from which the invention is made and showing the distal cutting flutes of FIG. 1.

FIG. 1 shows an exemplary embodiment 10 of the threaded intramedullary nail of the present invention. The nail 10 may be formed of any suitable biocompatible material, such as surgical grade stainless steel, titanium, alloys of nickel and chromium, nitinol, PEEK, hydroxyapatite, bioglass or other bio compatible materials or combinations of these materials. The nail 10 has a first end, or proximal end, 12, a second end, or distal end, 14, a shaft 16 with an outer surface 17, and a center portion 18 between first end 12 and second end 14. A cutting end 19 with a bevel and two, three or four teeth 19a is provided at the trailing end 14 (which is distal relative to the torque driving recess but is implanted in the proximal portion of the metacarpal) and a driving surface 20 in a drive recess 22 is formed in the top of first end 12.

The cutting point 19 helps to cut through any bone left behind when the bone is drilled to receive device 10, and further include 2-5 equally radially spaced longitudinal cutting flutes 23 which extend lengthwise in the exterior surface and through the threads of the nail 10. The driving surface 20 in this embodiment has a hexalobe drive configuration, although any suitable driving configuration may be used. Other driving configurations that may be used include slotted, Pozidriv, Robertson, tri-wing, Torq-Set, Spanner Head, Triple Square and hex head.

Extending length wise in outer surface 17, preferably along the longitudinal axis of shaft 16, are grooves or cutting flutes 24. As used herein, "extending length wise" means that each groove 24 is elongated and extends along the shaft with one end of the groove nearer the first end 12 and the opposite end of the groove nearer the second end 14, but grooves 24 may be formed at an angle and not necessarily formed along the longitudinal axis shaft 16, although that is preferred. Grooves 24 preferably have edges that assist in boring the device 10 into and anchoring device 10 in the opening in a bone. Grooves 24 also may capture some debris left behind from the bone drilling process to create the opening created when device 10 is positioned into the opening.

The shaft 18 of the nail 10 of the present invention includes at least two sections of differing diameters, for example, a proximal section that extends for a length of from about 15% to 30% of the length of the device, and which is located at from 25% to 75%, and preferably at 55-65% of the distance of the length from the distal end of the device 10. Further, the device provides a cannulated cylindrical core or shaft 18 having an outer exterior surface 17 along its length, (which is provided in 5 mm increments from 35 to 75 mm) that defines an inner diameter relative to the lateral edge of a threaded portion which defines an outer diameter. The design includes one or more stepped portion which allow for a 0.25-1.0 mm increase in the proximal portion of at least the outer diameter or the inner diameter, and more preferably of both the outer diameter and the inner diameter. The transition area also includes longitudinal cutting flutes (2-5 of 3 to 10 mm length) to account for this increase at a length of the nail (i.e., from 25% to 75%, and preferably from 50% to 60%, of the distance of the length from the proximal end) which allows a clearance of the narrowed or "waisted" portion of the bone.

Figure 15:
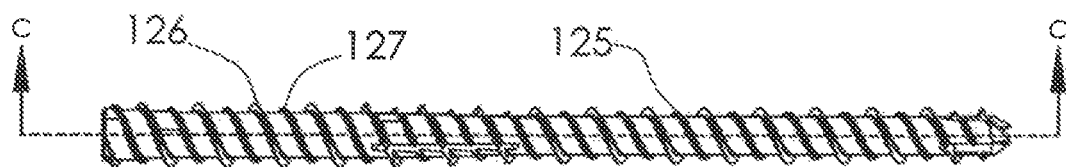
FIG. 15. is a side view of a second embodiment of the device of FIG. 1.
Figure 16:
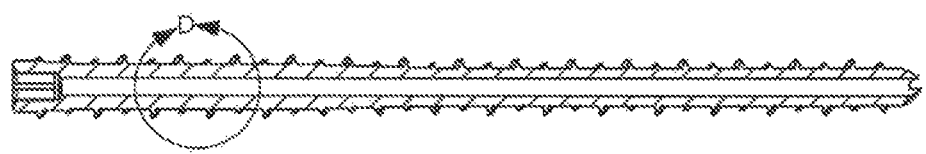
FIG. 16 is a cross-section of the device of FIG. 15 taken along line C-C.
Figure 17:
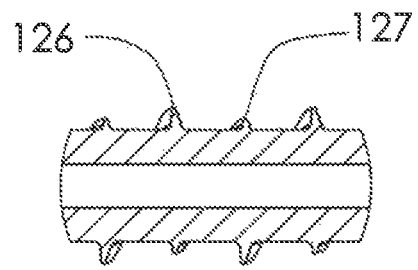
FIG. 17 is a detail of FIG. 16 showing the thread characteristics and a detail of the thread shape.
Figure 18:
FIG. 18 is a side view of the blank from which the invention is made and showing the transition section, the intermediate cutting flutes and distal cutting flutes of FIG. 15.
Figure 19:
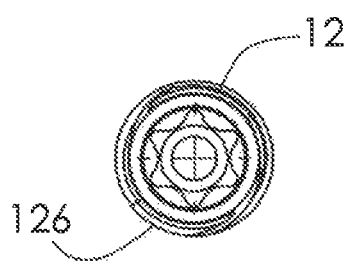
FIG. 19 is an end view of the proximal view of the device of FIG. 15.
Figure 20:
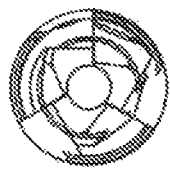
FIG. 20 is an end view of the distal tip of the device of FIG. 15.

The device includes a thread 25 which is defined between the outer diameter and the inner diameter and can suitably include a right-handed single start thread with a pitch of from 3 to 5 mm, and preferably at least 4.0+/−0.25 mm with a similar lead value. Alternatively, as is shown in FIGS. 15, 16 and 17, the device may include a double lead thread 125 having a first thread 126 and a second thread 127 of the same lead value with the second thread 127 having a height that is approximately 50% of the height of the first thread 126.

The leading and following flanks of the threads together form an angle of 5° to 60°, and preferably 15±10°, and are connected by a thread crest of length 0.05 to 0.2 mm which is separated from the root diameter by a thread depth of 0.2 mm to 0.8 mm.

Figure 9:
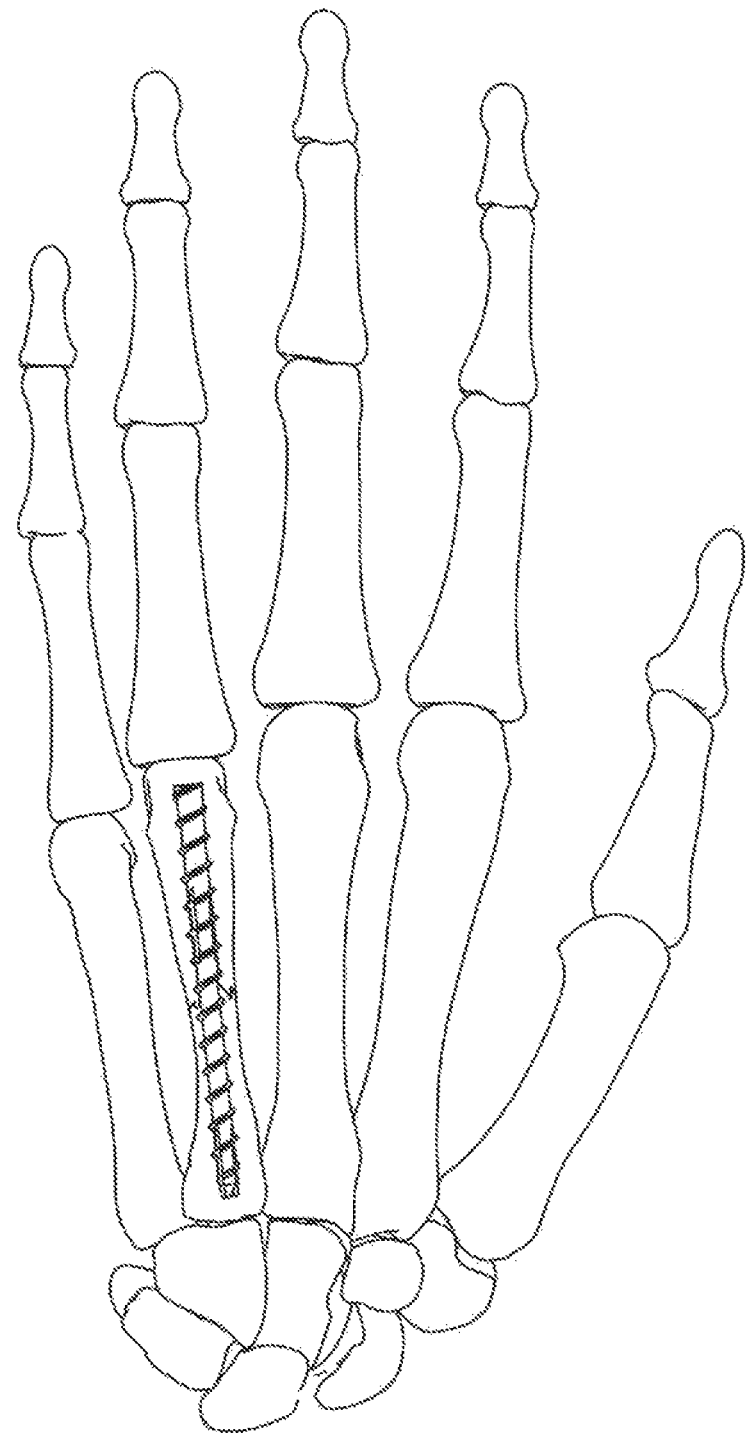
FIG. 9 is a top view of a skeleton of a hand showing the implant of the invention in place in a fractured metacarpal.

FIG. 9 illustrates a nail 10 in accordance with the present invention in position in a fourth metacarpal and securing a reduced fracture.

Figure 10:
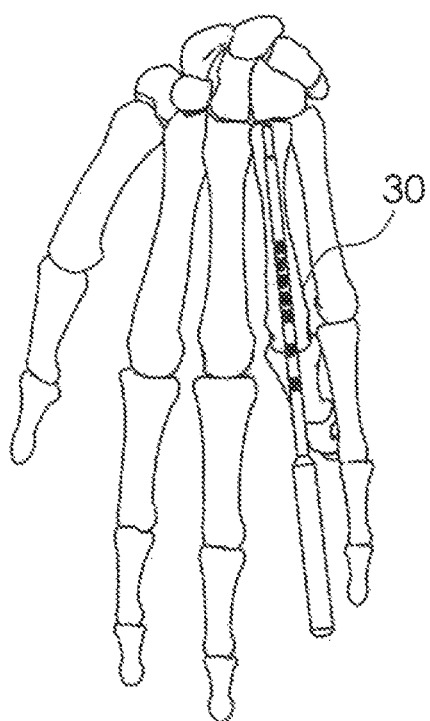
FIG. 10 is an illustration of the step of measuring a metacarpal for use with a technique in accordance with the invention.

In FIG. 10, in a first step of a surgical technique in accordance with the invention, the size of the metacarpal 30 at issue is determined in order to size the implant.

Figure 11:
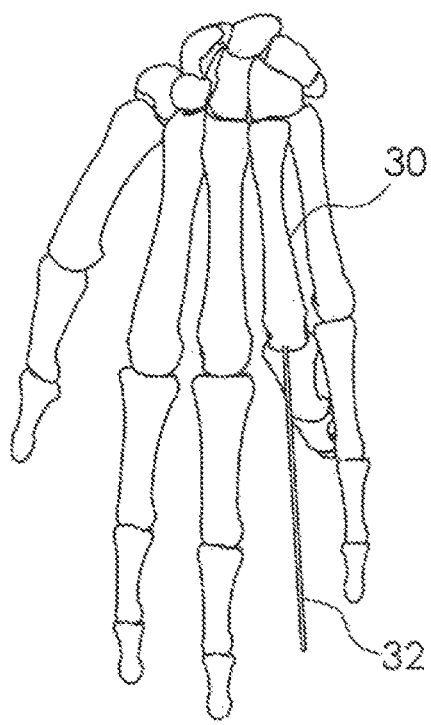
FIG. 11 is an illustration of the step of inserting a guide wire in a retrograde fashion to anatomically reduce the fracture fragments in accordance with the technique of the invention.

In FIG. 11, it is illustrated that the fracture in the bone is aligned and then a guide wire 32 is inserted in the intramedullary canal in retrograde.

Figure 12:
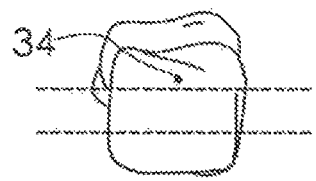
FIG. 12 is an illustration of the entry point of the guide wire of FIG. 11 in the dorsal third of the metacarpal head.

FIG. 12 illustrates the optimal position 34 for the insertion of the guide wire.

Figure 13:
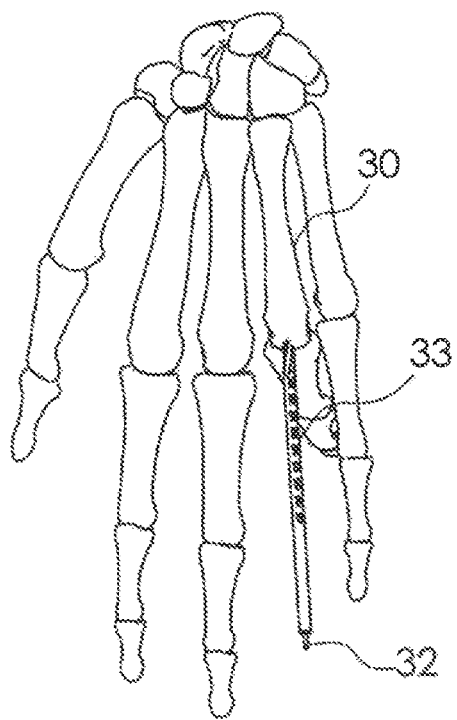
FIG. 13 is an illustration of the step of drilling by passing a cannulated drill over the guide wire.

In FIG. 13 a cannulated drill 33, uses the guide wire as a guide to drill an opening into the metacarpal bone which extends through the fracture and provides enough space on each side of the fracture to properly position device 10.

Figure 14:
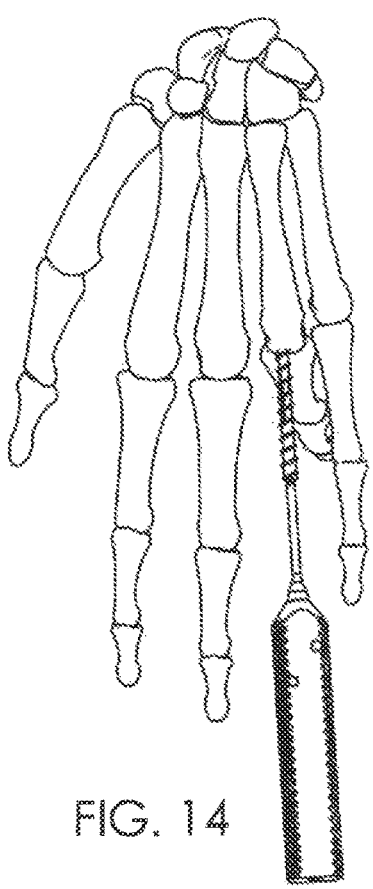
FIG. 14 is an illustration of the step of inserting the implant in the metacarpal in accordance with the surgical technique of the invention.

In FIG. 14, the device 10 is driven into the opening in the metacarpal bone by means of the drive recess. The outer diameter of the threads 28, is slightly larger than the inner diameter of the opening in the bone. This provides bone material for threads 28 to thread into and provides a tight fit for device 10.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

The invention is claimed as follows:

1. An intramedullary implant comprising:
   a first portion, the first portion extending about 28 to 30% of a length of the intramedullary implant;
   a second portion comprising one or more cutting flutes; and
   a center portion between the first portion and the second portion,
   wherein a driver recess is formed in a first end of the first portion,
   wherein a portion of the intramedullary implant comprises one or more cutting grooves extending along a longitudinal axis of the intramedullary implant,
   wherein a diameter of the second portion is 0.4 to 2 mm smaller than a diameter of the first portion,
   wherein the second portion comprises a double lead thread, and
   wherein a thread of the first portion and a thread of the second portion have the same pitch.

2. The intramedullary implant of claim 1, wherein the double lead thread comprises a first thread having a first pitch value and a second thread having a second pitch value.

3. The intramedullary implant of claim 2, wherein the first pitch value and the second pitch value are the same.

4. The intramedullary implant of claim 1, wherein the intramedullary implant comprises titanium.

5. The intramedullary implant of claim 1, wherein the intramedullary implant comprises stainless steel.

6. The intramedullary implant of claim 1, wherein the intramedullary implant is configured to be disposed in a scaphoid, capitellum, radial head, a metacarpal, a tarsal, a metatarsal, or an ulna.

7. The intramedullary implant of claim 1, wherein the length of the intramedullary implant is less than 130 mm.

8. The intramedullary implant of claim 1, wherein the intramedullary implant comprises a cannula.

9. The intramedullary implant of claim 8, wherein the cannula comprises a constant diameter along a length of the cannula.

10. The intramedullary implant of claim 1, wherein the second end portion comprises a plurality of radially spaced cutting flutes.

\* \* \* \* \*